United States Patent
Xiao et al.

(10) Patent No.: US 7,077,563 B2
(45) Date of Patent: Jul. 18, 2006

(54) DEPOSITION SENSOR BASED ON DIFFERENTIAL HEAT FLUX MEASUREMENT

(75) Inventors: Caibin Xiao, Harleysville, PA (US); David A. Little, Newtown, PA (US); Scott M. Boyette, New Hope, PA (US)

(73) Assignee: General Electric Company, Fairfield, CT (US)

( * ) Notice: Subject to any disclaimer, the term of this patent is extended or adjusted under 35 U.S.C. 154(b) by 0 days.

(21) Appl. No.: 10/717,154

(22) Filed: Nov. 19, 2003

(65) Prior Publication Data

US 2005/0105583 A1    May 19, 2005

(51) Int. Cl.
*G01K 17/00* (2006.01)
*G01K 17/08* (2006.01)
*G01K 1/16* (2006.01)
*G01N 25/44* (2006.01)

(52) U.S. Cl. .............................. 374/29; 374/7; 374/10; 374/57; 374/141

(58) Field of Classification Search .................... 374/4, 374/5, 10, 29–31, 43–45, 57, 141, 7, 11, 135, 374/179; 73/61.62
See application file for complete search history.

(56) References Cited

U.S. PATENT DOCUMENTS

| | | | | |
|---|---|---|---|---|
| 3,733,887 A | * | 5/1973 | Stanley et al. ................. | 374/44 |
| 3,834,873 A | * | 9/1974 | Picker ......................... | 436/147 |
| 4,138,878 A | * | 2/1979 | Holmes et al. ................. | 374/7 |
| 4,383,438 A | * | 5/1983 | Eaton .......................... | 73/61.62 |
| 4,408,568 A | * | 10/1983 | Wynnyckyj et al. ......... | 122/379 |
| 4,571,094 A | * | 2/1986 | Wynnyckyj et al. .......... | 374/29 |
| 4,577,976 A | * | 3/1986 | Hayashi et al. ............... | 374/29 |
| 4,595,297 A | * | 6/1986 | Liu et al. ...................... | 374/29 |
| 4,607,961 A | * | 8/1986 | Wynnyckyj et al. .......... | 374/30 |
| 4,722,610 A | * | 2/1988 | Levert et al. ................. | 374/43 |
| 4,729,667 A | | 3/1988 | Blangetti et al. | |
| 4,779,994 A | * | 10/1988 | Diller et al. .................. | 374/29 |
| 4,910,999 A | * | 3/1990 | Eaton ......................... | 73/61.62 |
| RE33,346 E | * | 9/1990 | Knudsen et al. ........... | 73/53.01 |
| 5,171,518 A | | 12/1992 | Barshay et al. | |
| 5,429,178 A | * | 7/1995 | Garey et al. ................ | 165/11.1 |
| 5,590,706 A | | 1/1997 | Tsou et al. | |
| 5,855,791 A | * | 1/1999 | Hays et al. .................. | 210/696 |

(Continued)

FOREIGN PATENT DOCUMENTS

DE    197 21 810 A1    12/1998

(Continued)

OTHER PUBLICATIONS

Characklis, W.G., "A Rational Approach to Problems of Fouling Deposition," *Fouling of Heat Exchangers Surfaces*, R.W. Bryers, ed., United Engineering Trustees, Inc., pp. 1-31, 1983.

(Continued)

*Primary Examiner*—Gail Verbitsky
(74) *Attorney, Agent, or Firm*—Wegman, Hessler & Vanderburg (57) ABSTRACT

An apparatus and method for the monitoring and measurement of chemical and/or biological deposition in heat exchangers and other fluid processing vessels. The new and original sensing system includes at least two hollow fluid vessels conductively mounted across a constant heat transfer path. Thin film heat flux sensors are attached to a heat transfer surface of the vessels in order to measure changes in differential heat flux that occur when deposition begins to accumulate in the vessel. In this way, it is shown that differential heat flux measurements can be used to detect and measure the early onset of chemical and/or biological deposition.

25 Claims, 7 Drawing Sheets

U.S. PATENT DOCUMENTS

| | | | |
|---|---|---|---|
| 6,062,069 A * | 5/2000 | Panchal et al. | 73/53.01 |
| 6,219,573 B1 * | 4/2001 | Pompei | 600/474 |
| 6,238,085 B1 * | 5/2001 | Higashi et al. | 374/10 |
| 6,241,383 B1 * | 6/2001 | Feller et al. | 374/40 |
| 6,264,362 B1 * | 7/2001 | Rolston | 374/29 |
| 6,390,669 B1 * | 5/2002 | Nakamura et al. | 374/12 |
| 6,499,876 B1 | 12/2002 | Baginksi et al. | |
| 6,508,585 B1 * | 1/2003 | Nakamura et al. | 374/12 |
| 6,575,662 B1 * | 6/2003 | French | 405/80 |
| 2005/0105584 A1 * | 5/2005 | Ichikawa et al. | 374/44 |
| 2006/0032606 A1 * | 2/2006 | Thybo et al. | 165/11.1 |

FOREIGN PATENT DOCUMENTS

| | | |
|---|---|---|
| EP | 0155 826 A2 | 9/1985 |
| FR | 2 422 929 | 11/1979 |
| JP | 60228946 A * | 11/1985 |
| WO | WO 43762 A1 * | 7/2000 |

OTHER PUBLICATIONS

Jones, A.D. et al., "The Use of a Heat Flux Sensors in Monitoring Fouling," proceedings of conference held at Jesus College, Cambridge, edited by Fryer, Hasting, and Jeurnink, European Commission DGXII, Science, Research and Development, pp. 230-241, Mar. 23-25, 1994.

Lingfang, S. et al., "Development of a New Online Montoring Systems about Anti-fouling Efficiency of Cooling Water Treatment Technology," *Proceedings of the 4th World Congress on Intelligent Control and Automation*, Shanghai, P.R. China, pp. 3179-3181, Jun. 10-14, 2002.

"Dats Side-Stream Fouling Monitor Systems," Website Product Page, Bridger Scientific, Inc., Sandwich, MA, pp. 1-2, Sep. 29, 2003.

* cited by examiner

DEPOSITION SENSOR BASED ON DIFFERENTIAL HEAT FLUX MEASUREMENT

FIELD OF INVENTION

The invention pertains generally to the monitoring of mineral and biofilm deposition in industrial fluid processing vessels and in particular relates to a method and apparatus for the early detection and measurement of deposit accumulation.

BACKGROUND OF THE INVENTION

Chemical and/or biological deposition in industrial process fluid adversely affects processing efficiency and can force operational downtime or even plant shutdown. It is well known in the art that mineral and/or biofilm deposition in cooling towers, heat exchangers, or other fluid processing vessels reduces critical heat transfer efficiency, decreases flow velocity, and can lead to structure fatigue and crack formation. Moreover, the maintenance of service water heat exchanger performance is a safety issue for utility plants, especially nuclear power plants. Quite obviously then, there is a need to provide for the accurate and timely detection and measurement of chemical and/or biological deposit accumulation in industrial process fluid and processing vessels.

Traditionally, the onset of deposition in industrial process fluid has been monitored by measuring either the temperature difference across a heat transfer surface or by measuring physical and chemical changes caused by deposition on a clean surface immersed in the fluid by way of electrochemical, optical, spectroscopic, or acoustic methods. Several monitoring systems based on temperature measurement have been used to monitor mineral and biofilm deposition, especially in cooling towers and heat exchangers. The heat transfer surface in many of these systems is simulated by electric heat. These systems are usually easy to set up and operate. They provide heat transfer resistance values for the simulated heat transfer surface, which can be correlated to the overall heat transfer efficiency of heat exchangers. However, deposit monitoring based on temperature measurement is subject to process variations such as changes in process temperature, flow velocity, and environmental temperature. Additionally changes in power supply to the electric heater in a side stream heat flux simulator can cause similar errors. This is why commercially available deposit monitoring systems lack the sensitivity required to detect the early onset of deposit accumulation. Consequently, detecting the early onset of deposit accumulation in a cost effective manner has been heretofore difficult to achieve.

Methods used to measure the physical and chemical changes caused by deposition include optical transmittance, fluorescence, and quartz crystal microbalance. The sensitivity of these methods is usually high. However, these methods require relatively expensive instruments. Variations and process parameters affect the measurements, and a heat transfer surface may not be easily incorporated.

The foregoing has outlined a need for an improved system for the monitoring and measurement of deposit accumulation in industrial process fluids and fluid transport vessels. It is therefore desirable to have a fast, accurate, and cost-effective system that is capable of detecting and measuring the early onset of chemical and/or biological deposition.

SUMMARY OF THE INVENTION

The present invention provides an apparatus and method wherein differential heat flux measurements are used to detect the early onset of deposit accumulation in fluid processing vessels. In this system, a clean heat transfer surface is used as a reference heat transfer path, thereby allowing the differential heat flux measurement. The differential heat flux is used to measure changes in heat transfer resistance across a heat transfer surface. In this way, differential heat flux measurements are used to indicate the early onset of deposition and to quantify the deposition accumulation.

The invention will be described further in conjunction with the attached drawings and following detailed description.

DETAILED DESCRIPTION

In accordance with the present invention, it has been discovered that differential heat flux is significantly more sensitive to changes in heat transfer characteristics than traditional approaches based primarily on temperature measurements. The concept of the present invention is derived from the fact that measuring a small differential change in temperature is much more difficult than directly measuring differential changes in heat flux due to a change in heat transfer resistance. Changes in heat transfer resistance occur when deposits begin to accumulate inside the fluid or vessel under inspection. Since deposit accumulation leads to a change in the heat transfer resistance of the pertinent heat transfer surface, it is possible to detect the onset of deposit accumulation by measuring differential changes in heat flux that occur between the respective heat transfer surfaces. Accordingly, instead of measuring or inferring the temperature difference across a fouling surface as in traditional methods, the present invention involves measurement of differential heat flux between a reference surface and a fouling surface in order to detect and quantify deposit accumulation at such fouling surface.

Figure 1:
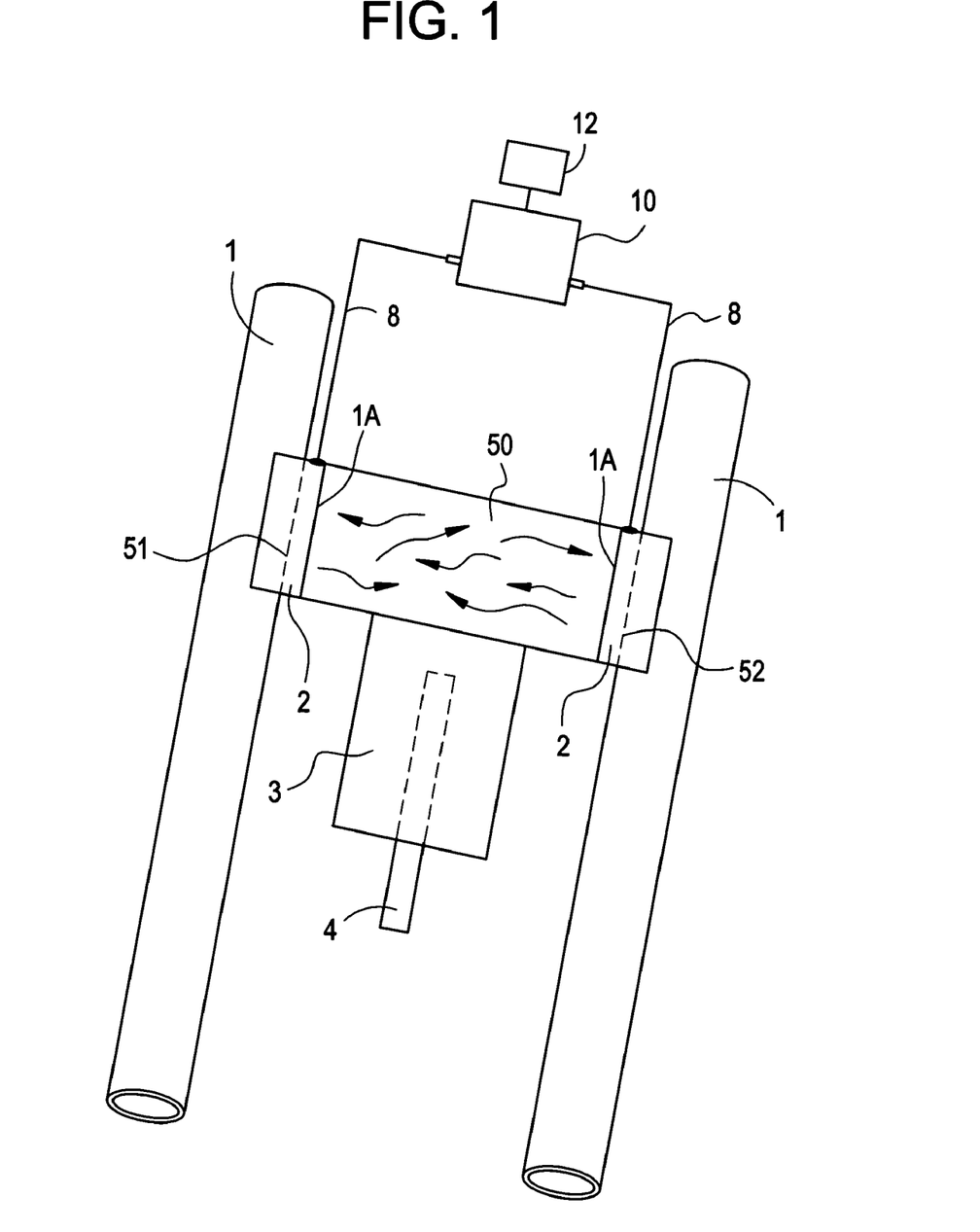
FIG. 1 is a perspective view of a deposition sensor system according to an embodiment of the present invention.

With reference now to the drawings, FIG. 1 shows a basic deposition sensor in accordance with an embodiment of the invention. The system generally comprises a pair of hollow vessels 1, a pair of heat flux sensors 2, a mounting unit 3, and a cartridge heater 4 as best shown in FIG. 1. By way of example, and not by way of limitation, the mounting unit 3 was made of a 2.5-inch diameter aluminum bar stock, machined down to 1-inch diameter on one end. Referring again to FIG. 1, a hole was drilled on the smaller end to accept the cartridge heater. The larger end of the aluminum block has two diametrically opposed, 0.805-inch diameter cutouts 1A.

Figure 2:
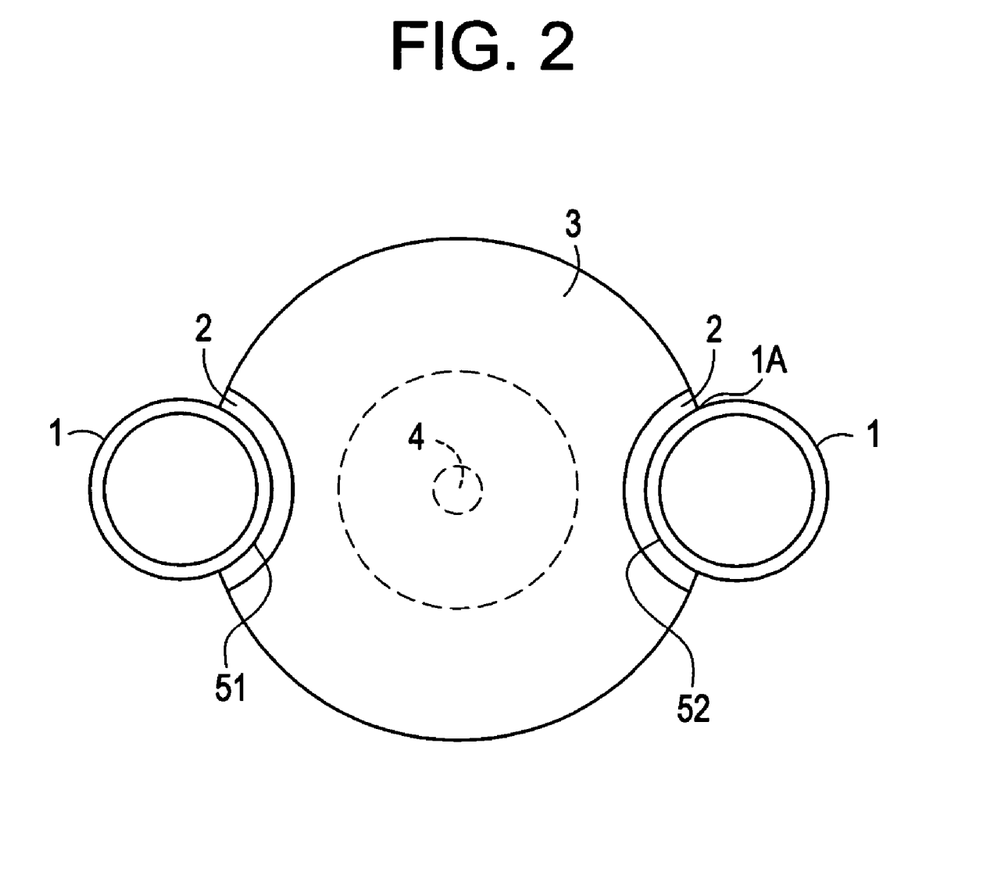
FIG. 2 is a top view of a deposition sensor system according to an embodiment of the present invention.

As best shown in FIG. 2, both vessels 1 comprise a stainless steel tube (20-inch long, 0.75-inch outside diameter, and 0.675-inch inside diameter). Each vessel is conductively mounted onto the mounting unit 3 by way of the respective cutouts 1A. The vessels are fastened in place by metal strip clamps (not shown). The exemplary illustration in FIG. 2 shows that each heat flux sensor 2 is mounted between an outside wall of the vessel and the respective cutout 1A. Accordingly, the present embodiment provides a pair of heat transfer surfaces 51 and 52 that are in thermal communication with heat transfer path 50. A heat conducting epoxy resin (not shown) was applied to both sides of the heat flux sensors, and the whole sensor assembly was insulated with commercially available insulating materials (not shown) to minimize heat loss. Skilled artisans will appreciate that many variations of the above sensor design are possible to achieve the same results. In this regard, it is contemplated that the heat flux sensors may be mounted to a variety of different shapes or surfaces, for example flat surfaces.

Referring again to FIG. 1, the two heat flux sensors 2 were purchased from Omega Engineering Inc. The sensors generate an electrical signal indicative of changes in heat flux measured at the heat transfer surfaces 51, 52. The sensors can be connected via wire 8 to a signal processing unit 10 and display unit 12, as shown in FIG. 1 to process and display the corresponding electrical signal generated by the sensors 2. As skilled artisans will appreciate, there are many alternative means, such as a computer based data acquisition system or a standard laboratory voltmeter that could be used to track and display the differential heat flux signal. For example, the electrical signal generated by the heat flux sensors can be transmitted to a microprocessor or other processor means that is effective to continuously calculate, record, and display the differential heat flux.

It is important to note that many variations in the above mentioned sensor design are possible to meet specific and varied customer needs. For example, design variations which are currently under investigation include: (1) different methods to introduce a heat transfer surface; (2) different methods to maintain a clean reference heat transfer surface; and (3) different geometric arrangements of the whole sensor assembly. Moreover, the heat source that could be used to introduce a heat transfer surface includes: (1) electric heat; (2) sonic or electromagnetic radiation heat (for example, laser induced); and (3) heat carrying process fluids.

Methods to generate a clean (reference) heat transfer surface include: (1) addition of a non-fouling fluid or solution containing acids or chemicals that can prevent biofouling or mineral deposition; (2) addition of a synthetic cooling solution that is well known to remain stable during heating operations; (3) generation of acids or oxidizing reagents with electrochemical cells; (4) introducing sonic or ultrasonic waves toward the reference surface in order to prevent and clean deposition formation; and (5) utilize automated brushing or other mechanical means such as flow excursion to clean away deposition inside the process tube. Another method contemplated by the present invention for generating a clean heat transfer surface includes the introduction of a small fraction (for example 1 ppm) of anti-fouling chemicals into the processing fluid exiting from the fouling tube. In this case, a small fraction of anit-fouling chemicals in combination with the processing fluid exiting from the fouling tube is effective to eliminate the accumulation of deposition without significantly changing flow rate, fluid temperature, or other processing parameters. Accordingly, such resulting non-fouling fluid may subsequently be utilized to generate a clean heat transfer surface.

Skilled artisans will appreciate that many variations in the above mentioned sensor designs are possible to meet specific and varied customer needs. For instance, the exemplary design described above covers variations in cleaning techniques that may be required to maintain a clean reference cell, but similarly, a clean reference cell can be provided by an electronic signal generated by a circuit that mimics a reference cell. Additionally, an electronic circuit can be designed that controls the heat transfer rate across the reference side by producing a constant heat loss, or that controls the reference side so that the total heat loss across the sensor assembly remains constant. Accordingly, it is not necessary to clean or dissolve deposition from the fluid vessel in order to achieve a guaranteed clean reference surface. A non-limiting example of this would be a finned array that provides constant heat loss across the reference sensor.

In operation, the fluid under investigation, such as the cooling water, flows through one of the hollow vessels, referred to as the fouling side. A reference fluid with a temperature close to that of the stream on the fouling side flows through the other hollow vessel, referred to as the reference side. The reference fluid required for this sensor could be the heat carrying process fluid or any non-fouling fluids recirculated by a temperature-controlled bath, or other means capable of achieving a reference heat transfer surface. In the best mode of operation contemplated at the time of invention, the reference stream corresponds to the cooling water stream from the fouling side of the sensor, except the chemical composition is slightly modified by online addition or generation of acids or any chemicals that prevent deposit formation on the reference side of the heat transfer surface. Here, a temperature bath is used to circulate deionized water through the reference tube.

In order to obtain a constant total heat flux in the system, voltage supplied to the cartridge heater 4 was adjusted to achieve a constant total input at the heat transfer path 50. Since no deposition is expected to occur on the reference side, the present system provides a clean reference surface which can be used to indicate changes in heat flux occurring at the fouling surface, thereby allowing differential heat flux measurement between the reference surface and the fouling surface to indicate the onset of deposition at the fouling surface.

Figure 5:
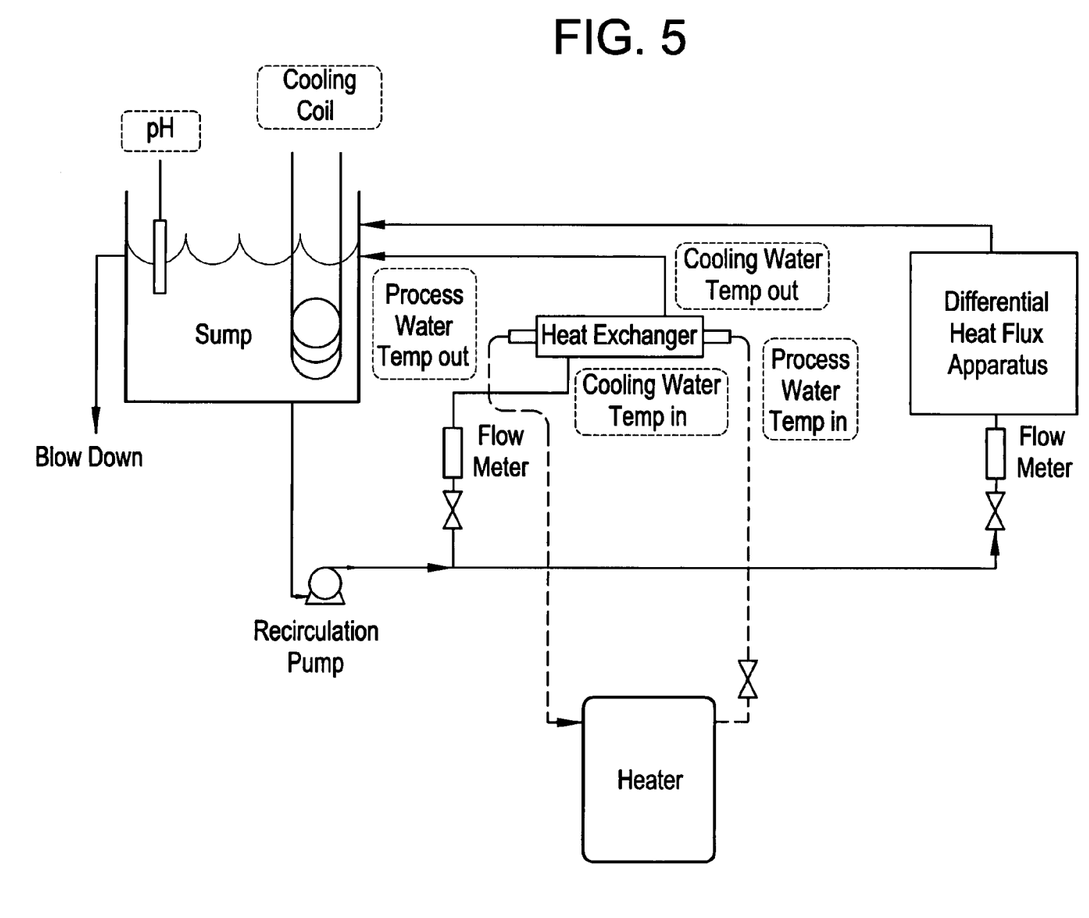
FIG. 5 is a schematic view of a model heat exchanger system used to evaluate the method and apparatus of the present invention.

The present sensor device was evaluated in a laboratory heat exchanger simulator shown in FIG. 5. The laboratory simulator utilizes a single pass shell and tube exchanger in a manner known in the art. The cooling water is on the shell side. The heat rejection is accomplished through a coil attached to a chiller. The process water (tube side) is heated by a 3 kW heater. The re-circulating flow was split so that the two measurement systems used identical water. The test was started with deionized water in the system. Hard water was added so that the water hardness gradually increased to concentrations where deposition is more likely. The test conditions are summarized in table 1 below. Cooling water and process water temperatures (inlet and outlet) were measured with four thermisitors. The heat transfer coefficient of this model cooling system was obtained from the four temperatures and of the cooling water and process water flow rates according to the standard method known in the art

TABLE 1

Test Conditions

| | |
|---|---|
| Inlet Cooling water temperature | 120.0° F. |
| Inlet Process water temperature | 140.0° F. |
| Cooling water flow rate | 4.1 gpm |
| Process water flow rate | 1.75 gpm |
| Contaminant feeding rates | $CaCl_2$: 10 ml/min |
| | Carbonate: 10 ml/min |
| $CaCl_2$ concentration | 1200 ppm as $CaCO_3$ |
| Carbonate | $Na_2CO_3$: 150 ppm |
| Re-circulation bath temperature | 120.2° F. |
| Reference-side flow rate | 1.0 gpm |
| Fouling-side flow rate | 5.0 gpm |

RESULTS AND DISCUSSION

It was discovered that for a given set of test parameters (bath and cooling water temperatures, flow rates, and heater wattage), $$Q_r = C \cdot Q_f \quad (1)$$

where $Q_r$ and $Q_f$ stand for heat flux across the reference and fouling sides of the heat transfer surfaces, respectively. C in equation 1 is a constant, which is approximately 1.0. This constant reflects asymmetry introduced during the construction of the deposition sensor and the difference in heat flux sensor sensitivities. This asymmetry can be measured using the initial values of $Q_r$ and $Q_f$ when no deposition is occurring in the fouling side of the apparatus.

With a constant voltage supplied to the heat cartridge, the total energy dissipating to the reference and fouling side streams is constant, $$Q_r + Q_f = Q_e \quad (2)$$

where $Q_e$ is the total heat energy provided by the cartridge heater less the energy lost to the environment through the insulation.

If any deposition occurs on the fouling side, $Q_r$ will no longer equal $C \cdot Q_f$, the difference in heat flux $\Delta Q_t$, $$\Delta Q_t = Q_r - C \cdot Q_f \quad (3)$$

is used to detect deposit accumulation.

Figure 3:
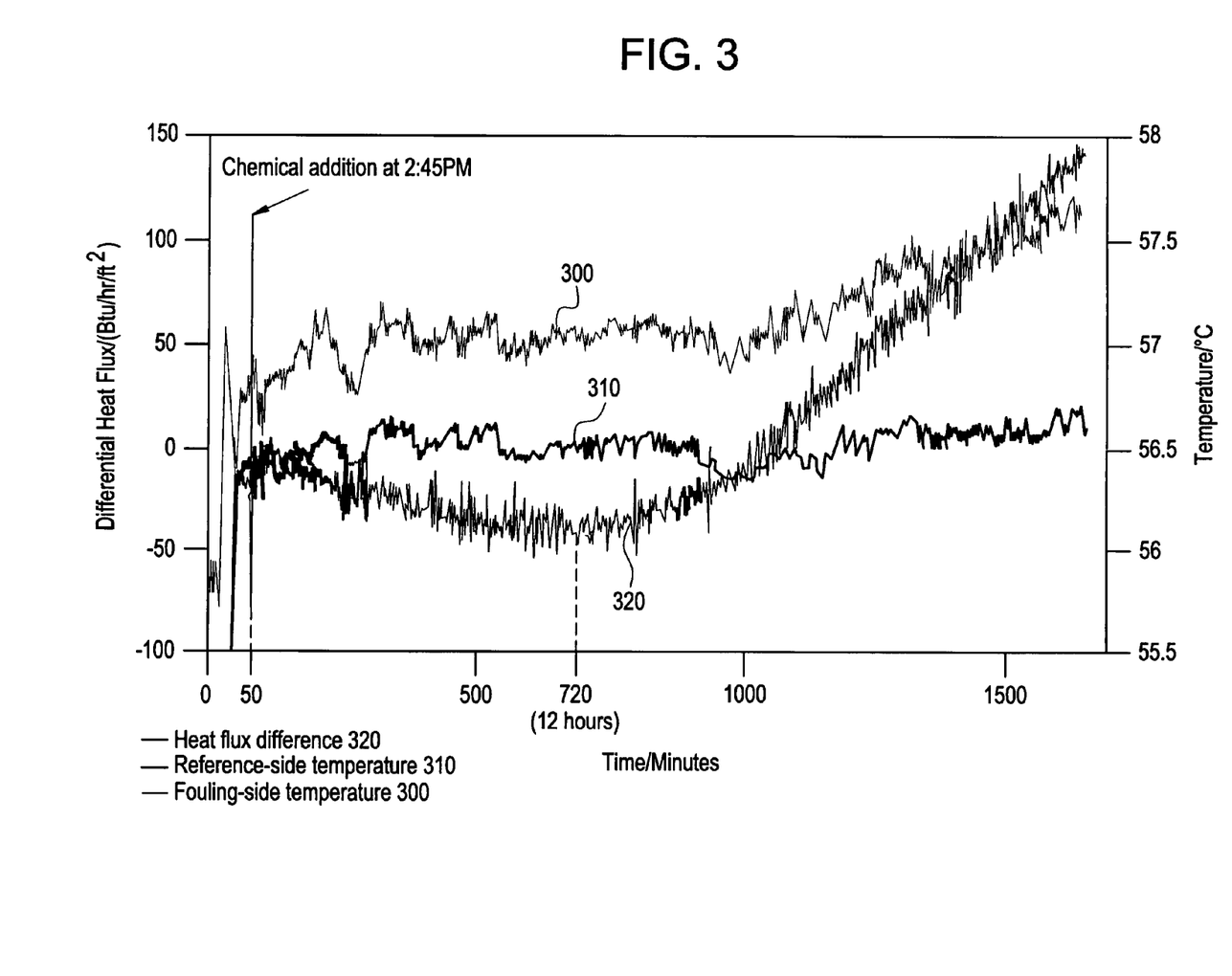
FIG. 3 is an example of temperatures and differential heat flux during $CaCO_3$ accumulation.
Figure 4:
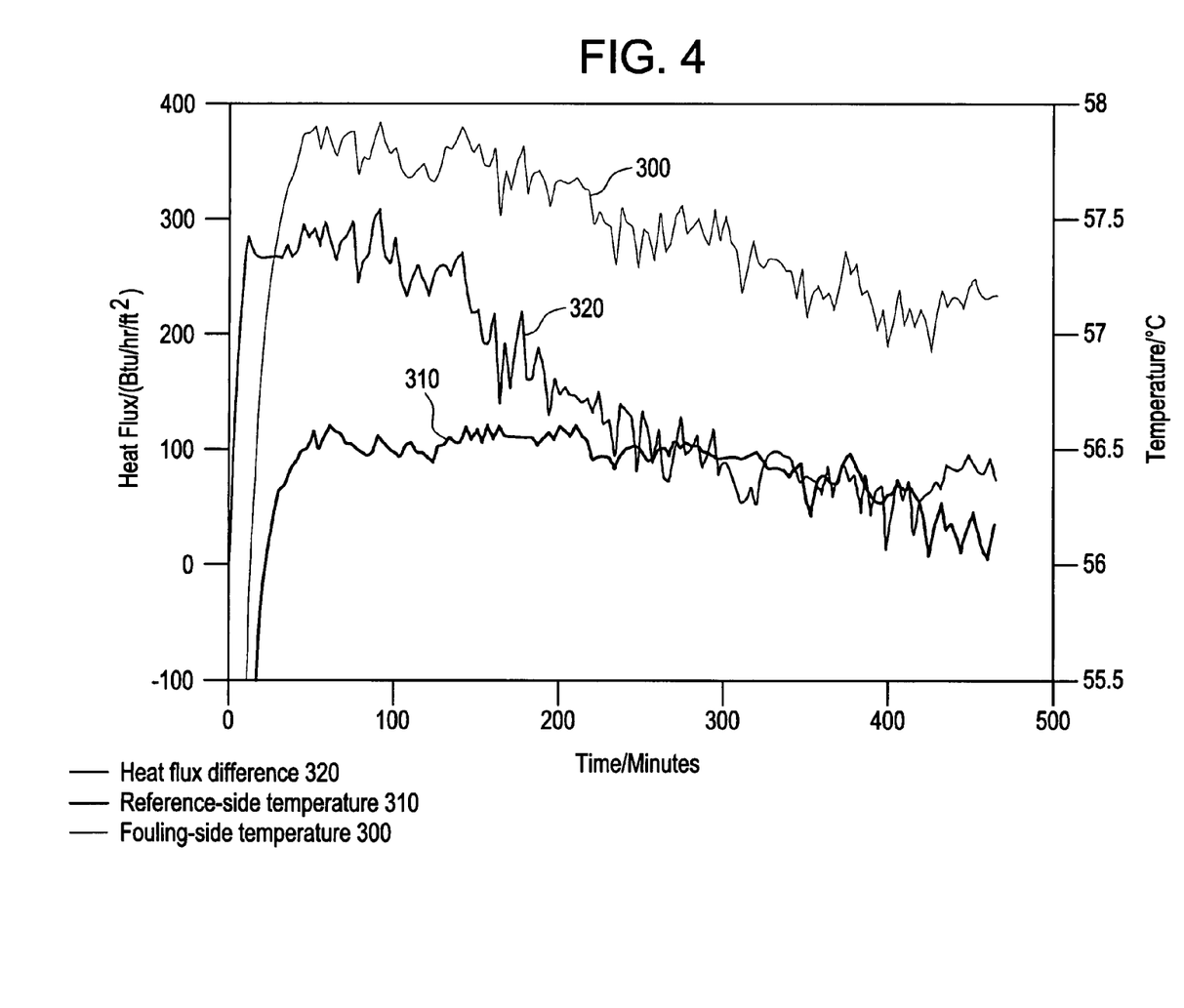
FIG. 4 is an example of temperatures and differential heat flux during $CaCO_3$ removal.

$\Delta Q_t$ and temperature measured by the heat flux sensor during calcium carbonate accumulation and removal are shown in FIGS. 3 and 4, respectively. Temperatures can also be measured directly by the thin-film heat flux sensors. The initial decrease in differential heat flux $\Delta Q_t$ (between approximately 0–50 minutes) indicates that heat transfer resistance decreases on the fouling side during this period. Decrease in heat transfer resistance in the early stage of deposit accumulation has been reported in many laboratory studies (A Rational Approach to Problems of Fouling Deposition, by W. G. Characklis, in Fouling of Heat Exchanger Surfaces, edited by R. W. Bryers, United Engineering Trustees, Inc., 1983) and is primarily attributable to initial turbulence in the system as is well known in the art, and thus can be discounted.

With reference again to FIGS. 3 and 4, there is illustratively shown the fouling side temperature 300 data, the reference side temperature 310 data, and the differential heat flux 320 data. As shown in FIG. 3, the differential heat flux ($\Delta Q_t$) 320 exhibits a shadow minimum about 720 minutes, or 12 hours, after the onset of calcium contaminant feeding in the system. This shadow minimum indicates the starting point of an upward trend in the slope of the differential heat flux 320. Accordingly, the shadow minimum corresponds to the starting time at which the accumulation of deposition in the system begins to clearly affect heat transfer resistance across the heat transfer surface. By comparison, the fouling side temperature 300 data does not begin to show a clear upward trend until about 1000 minutes after the start of calcium feeding. In other words, the differential heat flux measurement detects the onset of deposit accumulation in the system approximately 280 minutes sooner than with the traditional temperature based method.

Figure 6:
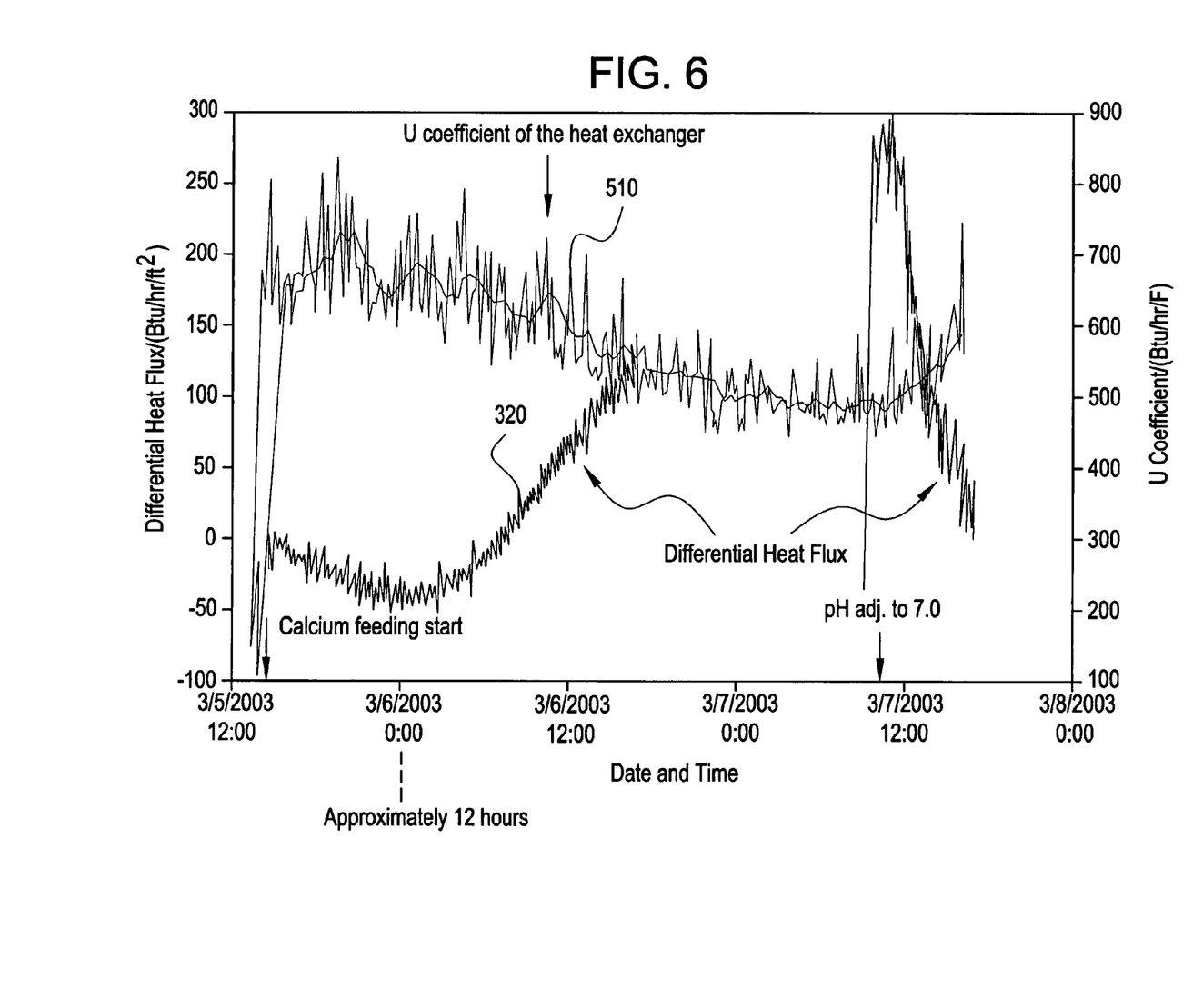
FIG. 6 is a trend comparison with U coefficient obtained from the temperature measurement.

FIG. 6 compares the trend in the differential heat flux 320 obtained from the current deposition sensor to the U coefficient 510 of the heat exchanger. This figure shows that the early onset of calcium carbonate deposition is detected by the differential heat flux ($\Delta Q_t$) sensor approximately 12 hours after the start of calcium feeding, while the traditional U coefficient measurement, based on temperature differences, does not provide the same clarity.

Figure 7:
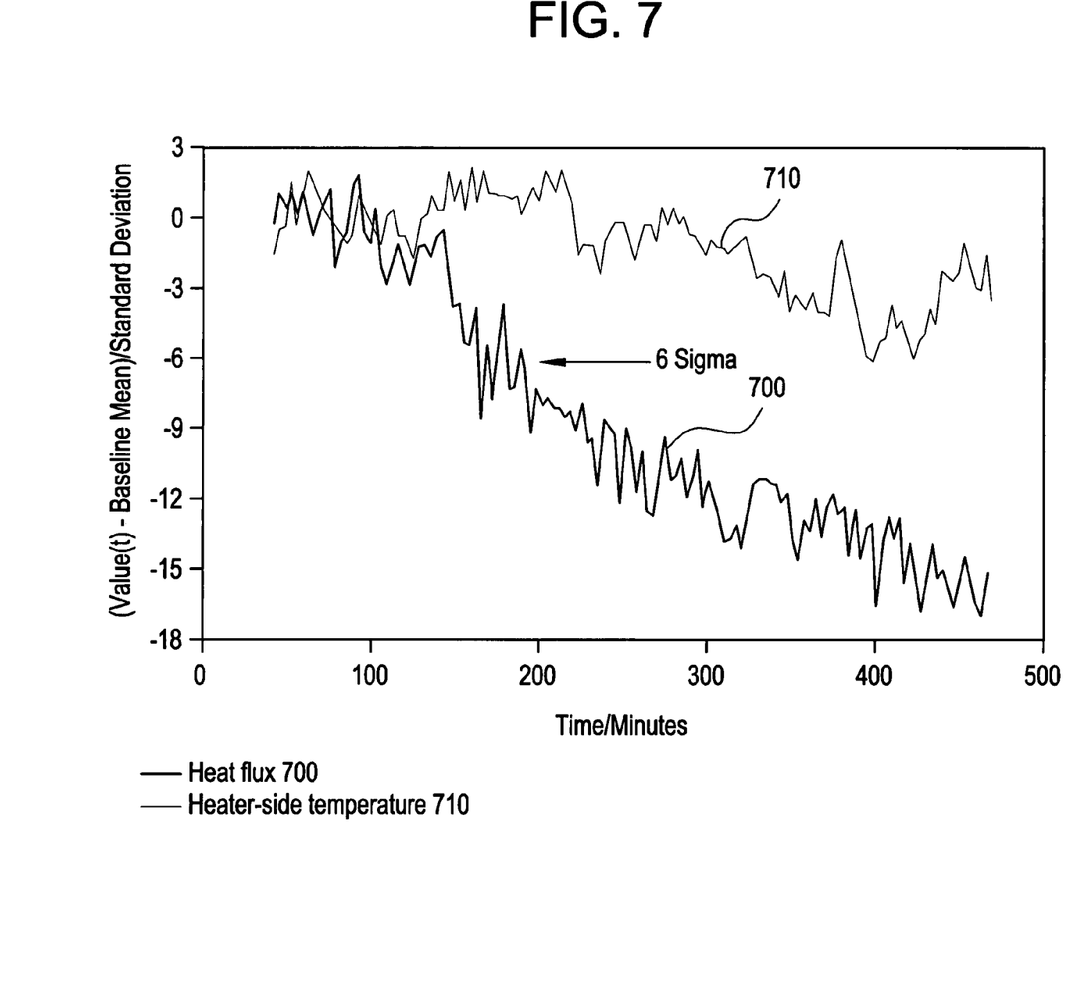
FIG. 7 is an example of differential heat flux and temperature changes relative to their baseline standard deviations.

In FIG. 7, changes in both heat flux $\Delta Q_t$ 700 and heater side temperature $T_w$ 710 during the deposit removal stage are presented relative to their standard deviations. It is clear that the differential heat flux $\Delta Q_t$ 700 is much more sensitive than the temperature $T_w$ 710 to changes in the cleanliness of the heat transfer surface.

Based on an equivalent electric circuit analysis and assuming that initial heat transfer resistances ($R_o$) on both sides are equal before any deposit accumulation, an approximate relationship can be derived:

$$\delta R/R_o \approx \Delta Q_t/Q_f \approx 2\Delta Q_t/Q_e \quad (5)$$

where $\delta R$ stands for the change in heat transfer resistance caused by deposition on the fouling side.

Note that it is the total heat flux $Q_e$ that is held constant, not $Q_f$ or $Q_r$. Variations in $Q_f$ can reflect process variations while variation in $Q_e$ are mainly caused by variation in the cartridge heater wattage. From equation 5, it is clear that the differential heat flux $\Delta Q_t$ can be used to indicate the early onset of deposition and to quantify the deposit accumulation.

The mean absolute deviation (MAD) of the 10-minute moving average of differential heat flux collected during $CaCO_3$ accumulation (FIG. 3) is 7.5 $Btu \cdot hr^{-1} \cdot ft^{-2}$ while the MAD of the baseline data shown in FIG. 1 is 7.0 $Btu \cdot hr^{-1} \cdot ft^{-2}$. The detection limit for the current deposition sensor was estimated at 0.23% (2*3*MAD/20000*100%) using equation 5 and a known $Q_e$ value of 20000 $Btu \cdot hr^{-1} \cdot ft^{-2}$. This suggests that the currrent deposition sensor is capable of measuring a 0.23% change in heat transfer resistance with a 95% confidence level.

While specific embodiments of the present invention have been described, it will be apparent to those skilled in the art that various modifications thereto can be made without departing from the spirit and scope of the invention as defined in the following claims.

What is claimed is:

1. A method for the measurement of differential heat flux, said method comprising the steps of:
   (a) providing a heat transfer reference surface;
   (b) providing a heat transfer fouling surface;
   (c) providing a heat transfer path capable of transferring heat flux between said reference surface and said fouling surface;
   (d) providing a pair of heat flux sensors, one of said sensors connected to said reference surface and the other one of said sensors connected to said fouling surface;
   (e) measuring heat flux values directly from each said sensor without having to measure temperature difference between said sensors;
   (f) calculating differential heat flux data across said heat transfer path from said heat flux values;
   (g) utilizing said differential heat flux data to detect and quantify deposit accumulation at said fouling surface; and
   wherein said heat flux values at said reference surface and said fouling surface both change in response to deposit accumulation at said fouling surface.

2. The method of claim 1 wherein said differential heat flux data is calculated according to the formula $\Delta Q_t = Q_r - C \cdot Q_f$.

3. The method of claim 1 wherein in cleaning of said reference surface is provided by mechanical brushing.

4. The method of claim 2 wherein cleaning of said reference surface is provided by mechanical brushing.

5. The method of claim 1 wherein sonic waves are used to keep said reference surface clean.

6. The method of claim 2 wherein sonic waves are used to keep said reference surface clean.

7. The method of claim 1 wherein said reference surface is kept clean by adding a solution to fluid flowing to said reference surface.

8. The method of claim 7 wherein said solution is synthetic cooling fluid.

9. The method of claim 1 further comprising the steps of:
   (a) generating a signal indicative of said heat flux data;
   (b) transmitting said signal to a microprocessor which continuously calculates, records, and displays said heat flux data.

10. The method of claim 2 further comprising the steps of:
    (a) generating a signal indicative of said heat flux data;
    (b) transmitting said signal to a microprocessor which continuously calculates, records, and displays said heat flux data.

11. The method of claim 3 further comprising the steps of:
    (a) generating a signal indicative of said heat flux data;
    (b) transmitting said signal to a microprocessor which continuously calculates, records, and displays said heat flux data.

12. The method of claim 4 further comprising the steps of:
    (a) generating a signal indicative of said heat flux data;
    (b) transmitting said signal to a microprocessor which continuously calculates, records, and displays said heat flux data.

13. The method of claim 5 further comprising the steps of:
    (a) generating a signal indicative of said heat flux data;
    (b) transmitting said signal to a microprocessor which continuously calculates, records, and displays said heat flux data.

14. The method of claim 6 further comprising the steps of:
    (a) generating a signal indicative of said heat flux data;
    (b) transmitting said signal to a microprocessor which continuously calculates, records, and displays said heat flux data.

15. The method of claim 7 further comprising the steps of:
    (a) generating a signal indicative of said heat flux data;
    (b) transmitting said signal to a microprocessor which continuously calculates, records, and displays said heat flux data.

16. The method of claim 8 further comprising the steps of:
    (a) generating a signal indicative of said heat flux data;
    (b) transmitting said signal to a microprocessor which continuously calculates, records, and displays said heat flux data.

17. The method of claim 1 wherein said heat flux sensors are thin-film heat flux sensors.

18. The method of claim 1 wherein said heat flux sensors are responsive to a flux of heat energy at said reference surface and said fouling surface.

19. The method of claim 1 wherein said reference surface is kept clean by generation of acids or oxidizing reagents with electrochemical cells.

20. The method of claim 7, wherein said solution is an acid or chemical which prevents bio-fouling or mineral deposition.

21. The method of claim 1 wherein said sensors are in thermal balance when said fouling surface is clean.

22. The method of claim 1 further comprising the step of providing a heating element for introducing a heat flux into said heat transfer path.

23. In a system for detecting deposit accumulation in heat-carrying fluid vessels comprising a heat transfer reference surface, a heat transfer fouling surface, a heat transfer path between said reference surface and said fouling surface, a pair of heat flux sensors, wherein one of said sensors is connected to said reference surface and the other one of said sensors is connected to said fouling surface, a method for measuring differential heat flux across said heat transfer path, said method comprising the steps of:
    (a) providing a heating element for introducing heat flux into said heat transfer path;

(b) transferring heat flux between said reference and fouling surfaces via said heat transfer path in response to deposit accumulation at said fouling surface;
(c) measuring heat flux values directly from each said sensor without having to measure temperature difference between said sensors;
(d) calculating differential heat flux data across said heat transfer path from said heat flux values;
(e) utilizing said differential heat flux data to detect and quantify said deposit accumulation at said fouling surface; and wherein said heat flux values at said reference surface and said fouling surface both change in response to said deposit accumulation.

24. The method of claim 23, wherein said sensors are in thermal balance when said fouling surface is clean.

25. The method of claim 23, wherein said heating element is independent from the heat source that provides heat energy to said heat-carrying fluid.

* * * * *

UNITED STATES PATENT AND TRADEMARK OFFICE
CERTIFICATE OF CORRECTION

PATENT NO.         : 7,077,563 B2
APPLICATION NO. : 10/717154
DATED              : July 18, 2006
INVENTOR(S)        : Caibin Xiao, David A. Little and Scott M. Boyette

Page 1 of 1

It is certified that error appears in the above-identified patent and that said Letters Patent is hereby corrected as shown below:

Column 7, line 54, please delete the word "in" after "wherein".

Signed and Sealed this

Third Day of October, 2006

JON W. DUDAS
*Director of the United States Patent and Trademark Office*